(12) United States Patent
Luo

(10) Patent No.: US 11,785,842 B2
(45) Date of Patent: Oct. 10, 2023

(54) N HETEROCYCLIC PLANAR PHOTOCOUPLER OUTPUT MATERIAL AND METHOD OF PREPARING THEREOF

(71) Applicant: WUHAN CHINA STAR OPTOELECTRONICS SEMICONDUCTOR DISPLAY TECHNOLOGY CO., LTD., Wuhan (CN)

(72) Inventor: Jiajia Luo, Wuhan (CN)

(73) Assignee: Wuhan China Star Optoelectronics Semiconductor Display Technology Co., Ltd., Hubei (CN)

( * ) Notice: Subject to any disclaimer, the term of this patent is extended or adjusted under 35 U.S.C. 154(b) by 380 days.

(21) Appl. No.: 16/762,146

(22) PCT Filed: Apr. 2, 2020

(86) PCT No.: PCT/CN2020/082939
§ 371 (c)(1),
(2) Date: May 7, 2020

(87) PCT Pub. No.: WO2021/057009
PCT Pub. Date: Apr. 1, 2021

(65) Prior Publication Data
US 2021/0408391 A1 Dec. 30, 2021

(30) Foreign Application Priority Data
Sep. 27, 2019 (CN) .......................... 201910921162.1

(51) Int. Cl.
C07D 239/26 (2006.01)
C07D 251/24 (2006.01)
(Continued)

(52) U.S. Cl.
CPC ......... H10K 85/654 (2023.02); C07D 239/26 (2013.01); C07D 251/24 (2013.01);
(Continued)

(58) Field of Classification Search
CPC ............. H01L 51/0067; H01L 51/0052; H01L 51/0072; H01L 51/5012; H01L 51/5262;
(Continued)

(56) References Cited

U.S. PATENT DOCUMENTS 6,229,012 B1 * 5/2001 Hu ....................... C07D 251/24
544/216
2008/0111473 A1 * 5/2008 Kawamura .......... C07D 213/24
428/917
(Continued)

FOREIGN PATENT DOCUMENTS

| JP | 2005276801 A | * | 10/2005 |
| JP | 2006225322 A | * | 8/2006 |
| JP | 2018135305 A | * | 8/2018 |

OTHER PUBLICATIONS

Chemical Abstract Service, STN Database [online], Registry No. 1229443-68-8 [Entered STN: Jul. 7, 2010]. (Year: 2010).*
(Continued)

Primary Examiner — Amanda L. Aguirre
(74) Attorney, Agent, or Firm — PV IP PC; Wei Te Chung; Zhigang Ma

(57) ABSTRACT

An N heterocyclic planar photocoupler output material is provided, and includes a structural formula as follows:

$R_1$—$R_2$—$R_1$.

The N heterocyclic planar photocoupler output material is selected from any one of following formula structures:

and (Continued)

The photocoupler output material has a very high "n" value, so that the top-emitting electroluminescent devices using it have achieved very high luminous efficiency. Therefore, it saves time and costs. Also, a method of preparing an N heterocyclic planar photocoupler output material is provided.

2 Claims, 1 Drawing Sheet

(51) Int. Cl.
| | |
|---|---|
| *C07D 401/14* | (2006.01) |
| *C09K 11/06* | (2006.01) |
| *H10K 85/60* | (2023.01) |
| *H10K 50/11* | (2023.01) |

(52) U.S. Cl.
CPC ............ *C07D 401/14* (2013.01); *C09K 11/06* (2013.01); *H10K 85/615* (2023.02); *H10K 85/6572* (2023.02); *C09K 2211/1018* (2013.01); *H10K 50/11* (2023.02)

(58) Field of Classification Search
CPC .. C07D 239/26; C07D 251/24; C07D 401/14; C09K 11/06; C09K 2211/1018
See application file for complete search history.

(56) References Cited

U.S. PATENT DOCUMENTS

2011/0240983 A1* 10/2011 Sekiguchi .............. H05B 33/14
257/40
2021/0408381 A1* 12/2021 Park ...................... C07C 211/54

OTHER PUBLICATIONS

Behmadi et al. J. Het. Chem. 2011, 48, 1117-1121. (Year: 2011).*
Yamakawa et al. JP 2006/225322 A English machine translation (online)(retrieved on Sep. 8, 2022 from <https://worldwide.espacenet.com/>) (Year: 2022).*
Aihara et al. JP 2018-135305A, English machine translation [online], accessed Jan. 18, 2023, retrieved from <https://www.j-platpat.inpit.go.jp> (Year: 2023).*

* cited by examiner

N HETEROCYCLIC PLANAR PHOTOCOUPLER OUTPUT MATERIAL AND METHOD OF PREPARING THEREOF

BACKGROUND OF INVENTION

Field of Invention

The present invention relates to the field of optoelectronic technology, and more particularly, to a photocoupler output material and a method of preparing thereof.

Description of Prior Art

Organic light emitting diode (OLED) displays have active light emission and do not require a backlight, and they also have high luminous efficiency, large viewing angles, fast response times, wide temperature adaptation, relatively simple production and processing technology, low driving voltage, low energy consumption, lighter, thinner, and flexible. Therefore, they have attracted many researchers, and dominant light emitting guest material is essential for OLEDs.

As for the currently top-emitting devices, microcavity effect may greatly improve device efficiency, narrow the spectrum, and widen the color gamut. In the devices, optical coupling output layer (CPL) plays an important role. A material with a high refractive index (N) may not only improve device efficiency, but also reduce thickness of the device to save materials and reduce costs.

SUMMARY OF INVENTION

In order to solve the above technical problems, the present invention provides a planar aromatic group as a bridge center, and both ends of the planar aromatic group connects other N heteroaromatic groups having narrow absorption bands. Also, A series of CPL materials having rod shapes modifies optical coupling output layer, and may be confirmed by mass spectrometry. Therefore, CPL materials is used to manufacture a series of high-performance OLEDs.

A series of high-performance OLEDs were prepared by confirming their structures by mass spectrometry and then applying these CPL materials to the light-emitting layer.

An N heterocyclic planar photocoupler output material comprises a structural formula as follows:

$R_1$—$R_2$—$R_1$. $R_1$ is selected from any one of following formula structures:

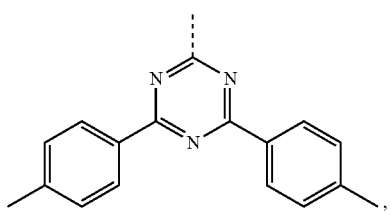

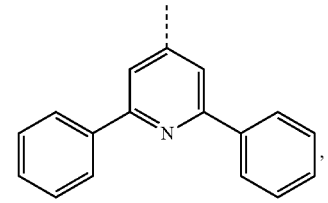

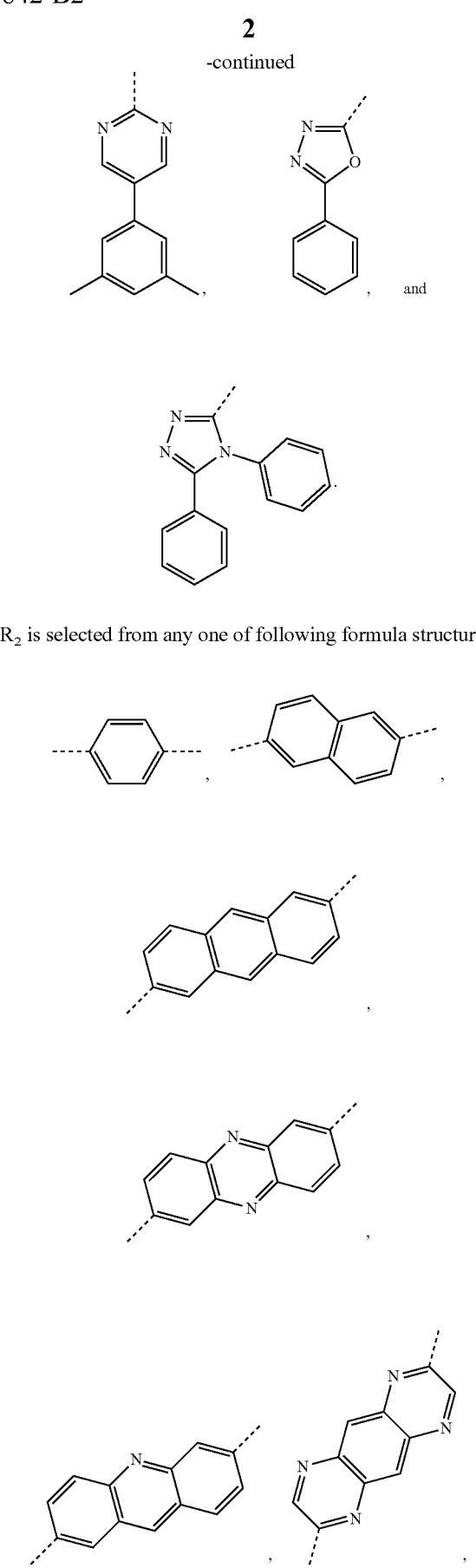

$R_2$ is selected from any one of following formula structures:

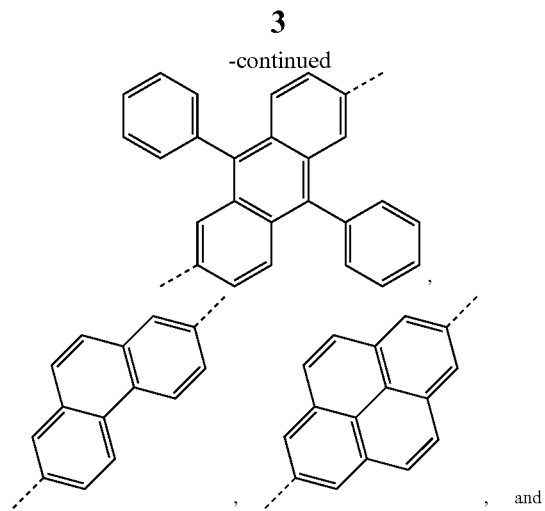
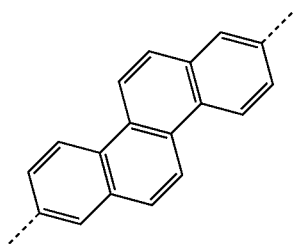
In one embodiment, the N heterocyclic planar photocoupler output material is selected from any one of following formula structures:
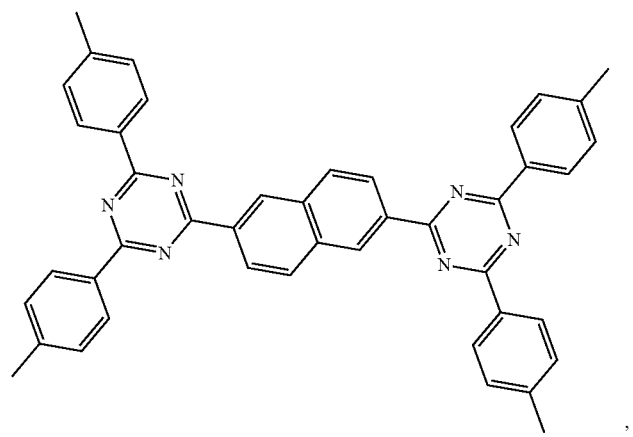
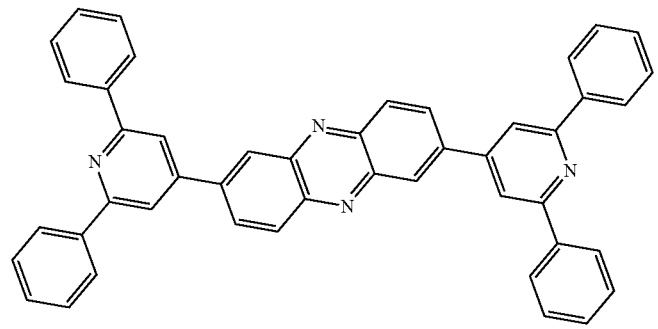
, and
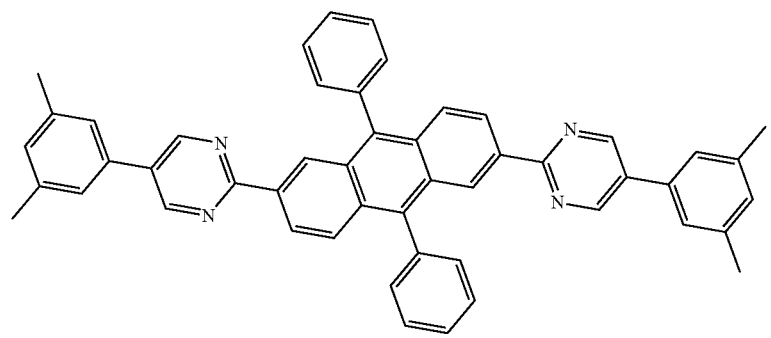

In one embodiment, synthetic raw materials for the N heterocyclic planar photocoupler output material comprises a first raw material comprising a $R_1$ group and a second raw material comprising a $R_2$ group. The $R_1$ group is selected from any one of following formula structures:

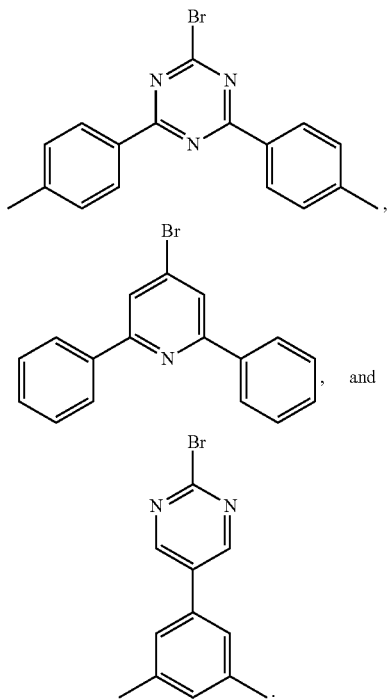

The $R_2$ group is selected from any one of following formula structures:

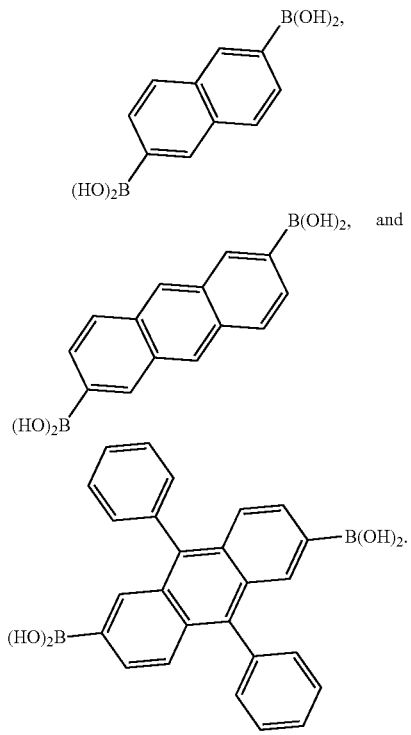

A method of preparing an N heterocyclic planar photocoupler output material comprises steps as follows:

step 1, adding a first raw material comprising a $R_1$ group and a second raw material comprising a $R_2$ group, Pd(dppf)Cl$_2$, and potassium acetate, and vacuuming for several times;

step 2, injecting deoxygenated N, N'-dimethylformamide under an argon atmosphere, reacting at 70° C. to 100° C. for 24 hours, and cooling to room temperature and forming a reacting solution;

step 3, pouring the reacting solution into ice water, extracting with dichloromethane for three times, combing an organic phase, and filling silica gel into a column; and step 4, purifying by column chromatography to obtain a blue powder.

In one embodiment, the first raw material comprising the $R_1$ group is selected from any one of following formula structures:

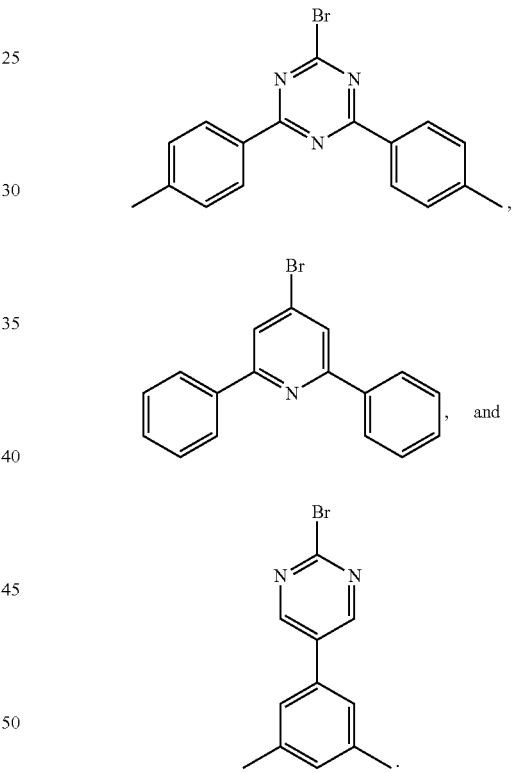

In one embodiment, the second raw material comprising the $R_2$ group is selected from any one of following formula structures:

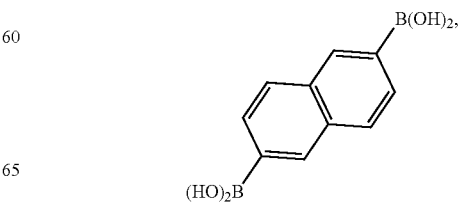

-continued

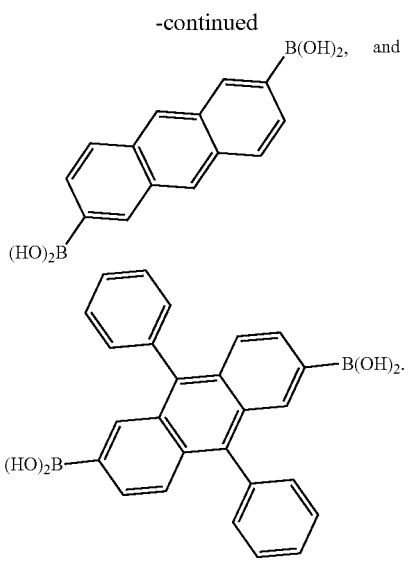

In one embodiment, the first raw material is present in an amount of 2.6 g to 3.4 g, and the first raw material is present in an amount of 10 mmol; and the second raw material is present in an amount 1.0 g to 2.1 g, and the second raw material is present in an amount of 5 mmol.

In one embodiment, in the step 2, the deoxygenated N, N'-dimethylformamide is injected under an argon atmosphere; and reacting at 80° C. for 24 hours, cooling to room temperature, and forming a reacting solution are performed.

In one embodiment, in the step 4, dichloromethane and n-hexane are added, a volume ratio of dichloromethane and n-hexane is 1:3, and purifying by column chromatography is performed.

In one embodiment, in the step 3, the reacting solution is poured into 200 ml ice water, extracting with dichloromethane for three times is performed, and combing an organic phase and filling silica gel into a column are performed.

Compared with the prior art, the general CPL material has a lower "n" value, and the thickness of the general CPL material used in the evaporation process exceeds 80 nm. In the present invention, the planar CPL molecular enables the CPL material to lie flat during the evaporation process, so that the CPL material has a very high "n" value. Accordingly, top-emitting electroluminescent devices having the CPL material have achieved very high luminous efficiency. At the same time, the thickness of the CPL in the device has been reduced from 85 nm to 65 nm, saving time and costs. Because the molecular arrangement is more orderly, the material has a higher refractive index, so when manufacturing OLED devices, the corresponding thickness of the CPL is reduced to 65 nm. Therefore, the amount of material is reduced, and CPL having high refractive index improves device efficiency.

DETAILED DESCRIPTION OF PREFERRED EMBODIMENTS

Figure 1:
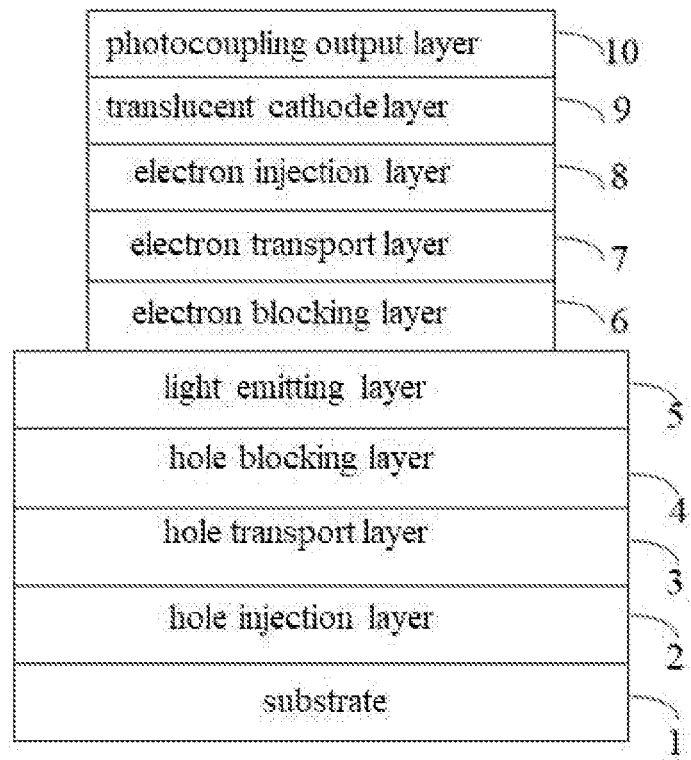
FIG. 1 is a schematic structural view of a top-emitting device according one embodiment of the present invention.
Figure 2:
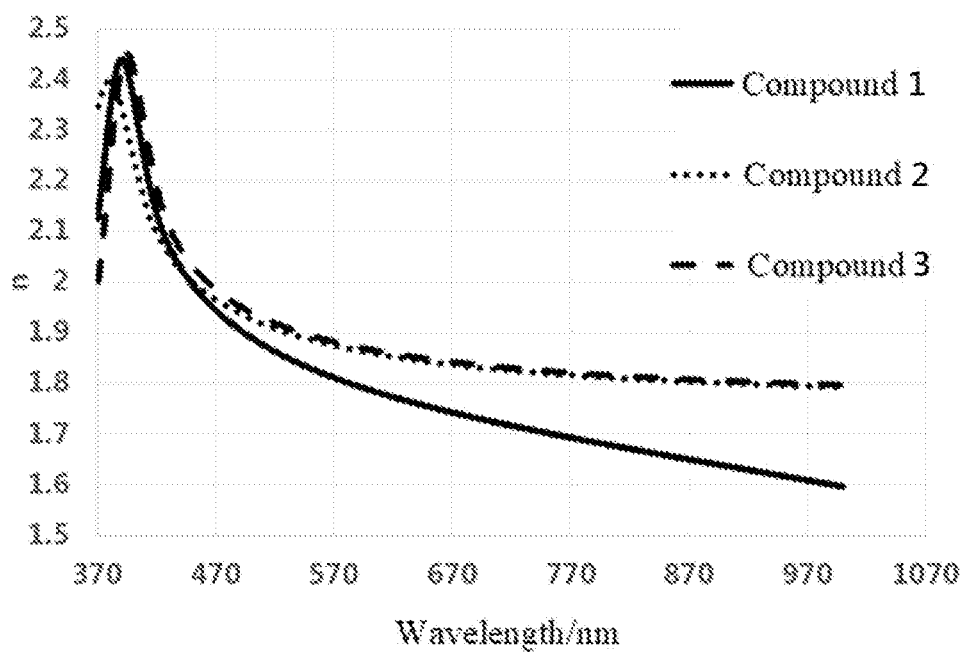
FIG. 2 is a curve diagram of "n" value of a target compound in an N heterocyclic planar photocoupler output material according to one embodiment the present invention.

The purpose of the present invention is to realize the synthesis of a planar CPL material having high "n" value and its application in a light emitting device. In order to achieve the purpose, An N heterocyclic planar photocoupler output material, comprising a structural formula as follows: $R_1$—$R_2$—$R_1$. $R_1$ is selected from any one of following formula structures:

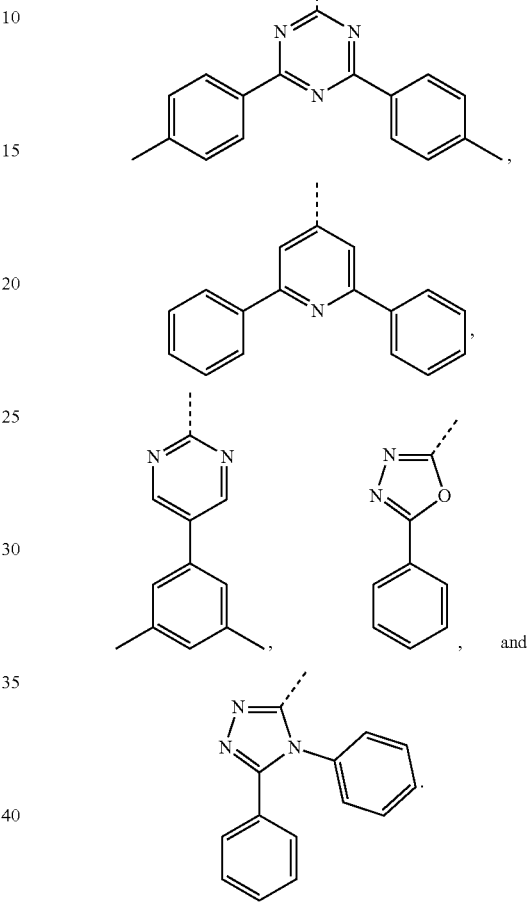

and $R_2$ is selected from any one of following formula structures:

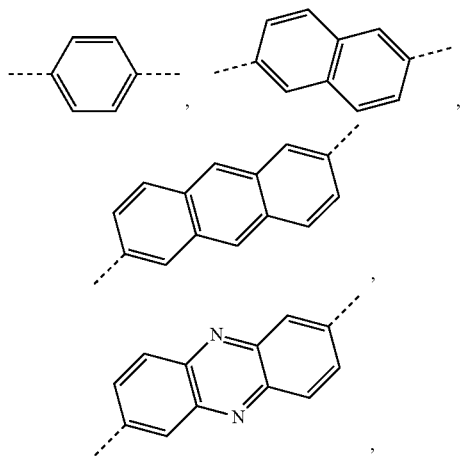

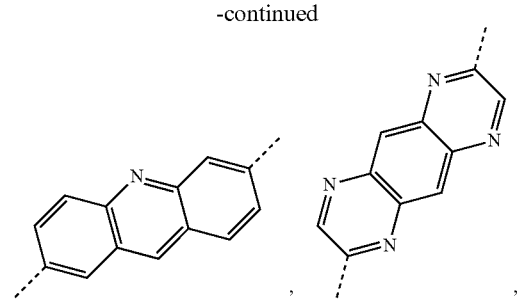

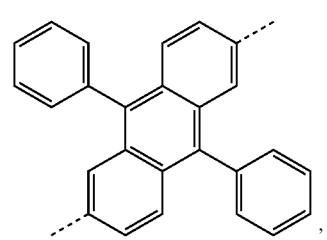

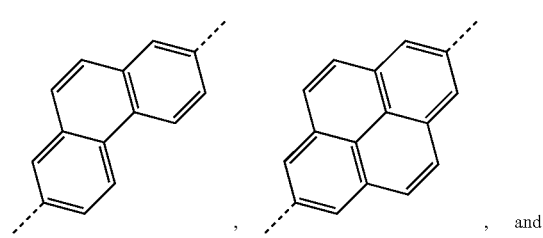

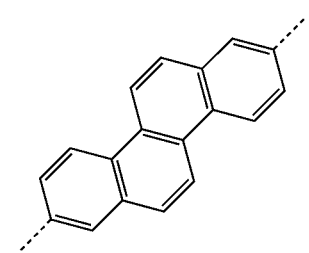

The N heterocyclic planar photocoupler output material is selected from any one of following formula structures:

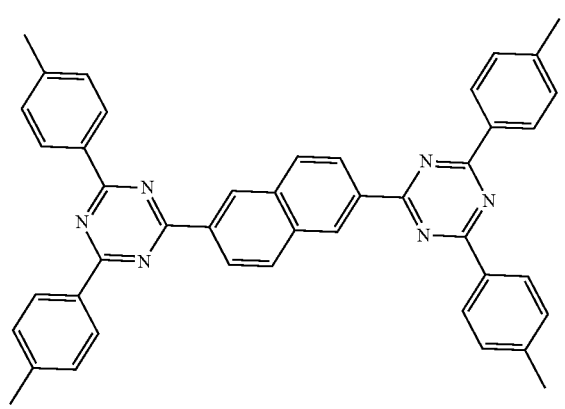

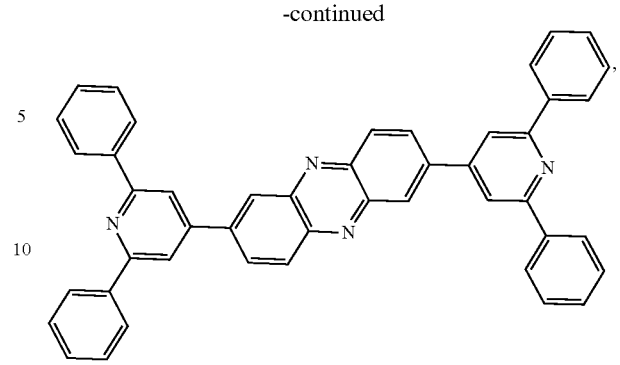

and

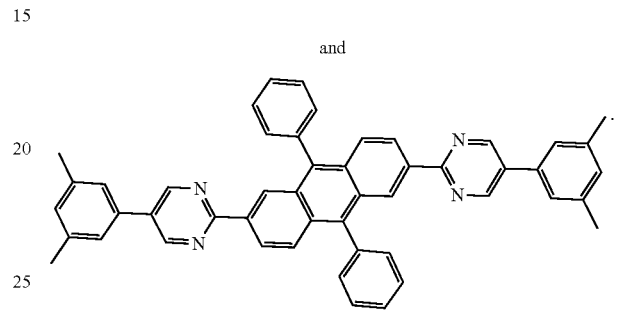

Preferably, the synthetic raw materials for the N heterocyclic planar photocoupler output material comprises a first raw material comprising a $R_1$ group and a second raw material comprising a $R_2$ group. The $R_1$ group is selected from any one of following formula structures:

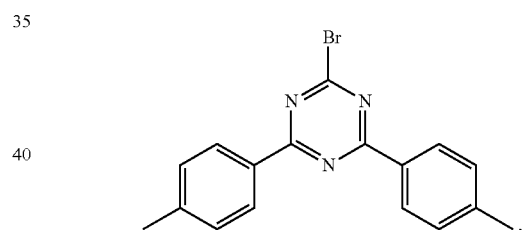

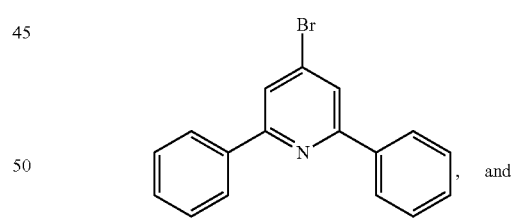, and

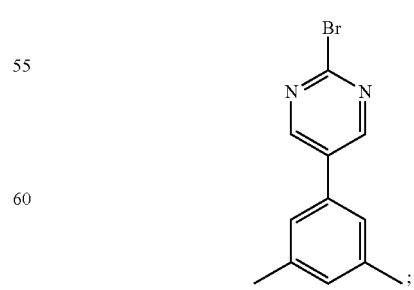;

and the $R_2$ group is selected from any one of following formula structures:

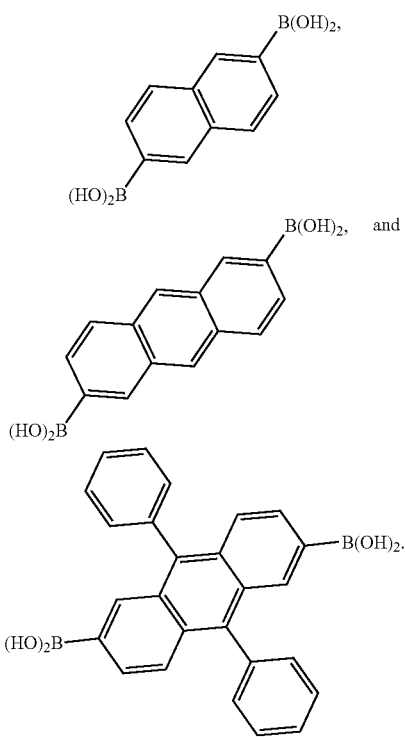
Correspondingly, specific raw materials are selected for specific products in the synthesis reaction.
In one embodiment,
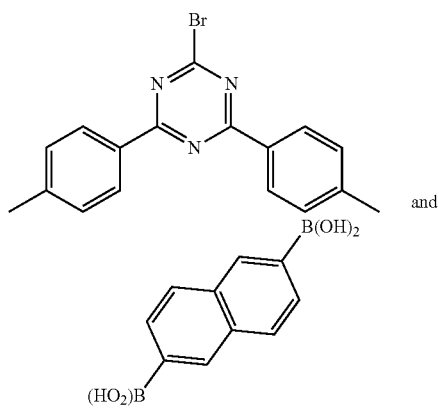
are raw materials and reacted to obtain
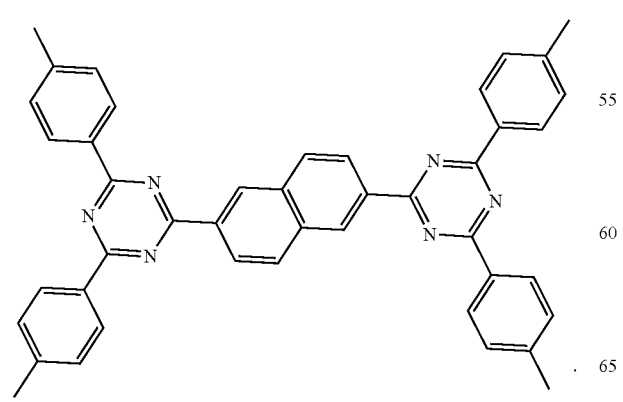
In one embodiment,
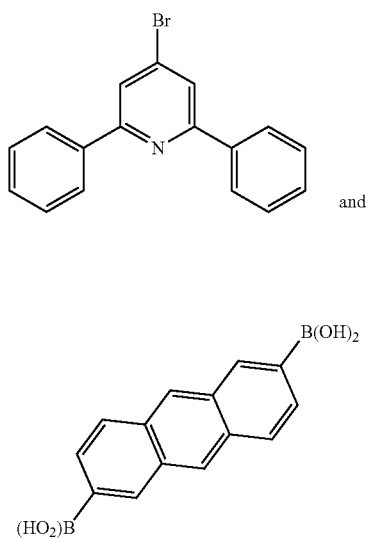
are raw materials and reacted to obtain
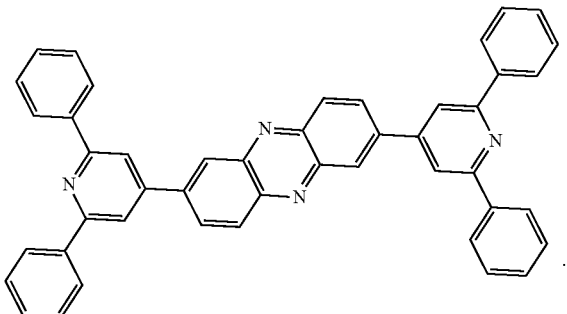
In one embodiment,
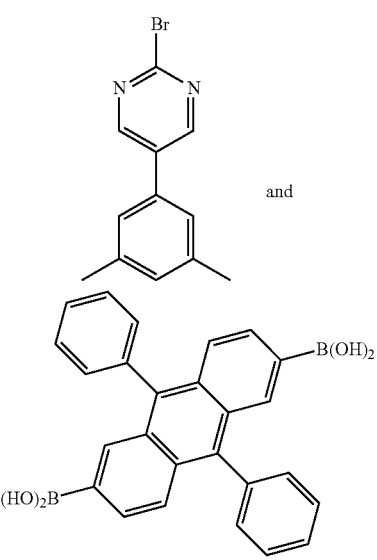

are raw materials and reacted to obtain

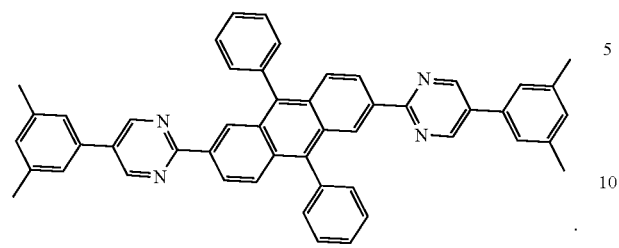

It should be note that the above-mentioned raw materials may be selected in any combination.

In addition, the first raw material is an electron-acceptor heterocyclic ring containing bromine, and the second raw material is a boric acid compound containing a large conjugate group, so that C—C may be coupled.

A method of preparing an N heterocyclic planar photocoupler output material comprises steps as follows:

step 1, adding a first raw material comprising $R_1$ group and a second raw material comprising a $R_2$ group, Pd(dppf)Cl$_2$, and potassium acetate, and vacuuming for several times;

step 2, injecting deoxygenated N, N'-dimethylformamide under an argon atmosphere, reacting at 70° C. to 100° C. for 24 hours, and cooling to room temperature and forming a reacting solution;

step 3, pouring the reacting solution into ice water, extracting with dichloromethane for three times, combing an organic phase, and filling silica gel into a column; and step 4, purifying by column chromatography to obtain a blue powder.

The first raw material comprising a $R_1$ group is selected from any one of following formula structures:

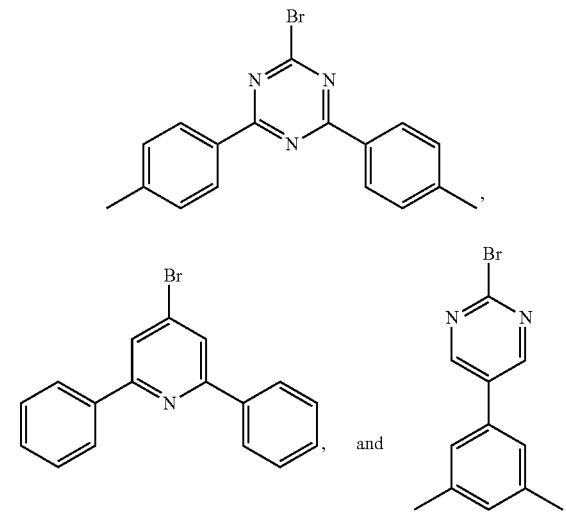

The second raw material comprising a $R_2$ group is selected from any one of following formula structures:

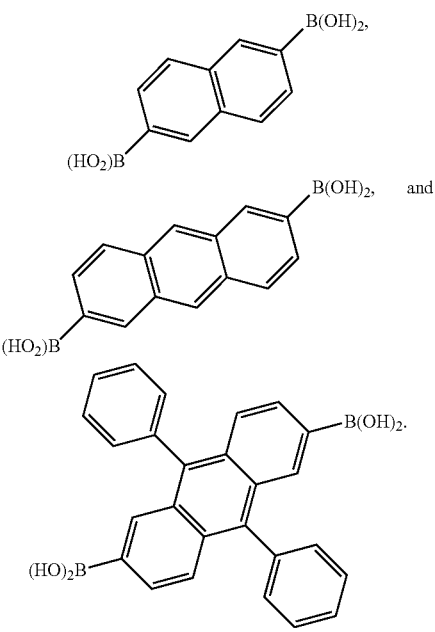

The N heterocyclic planar photocoupler output material is selected from any one of following formula structures:

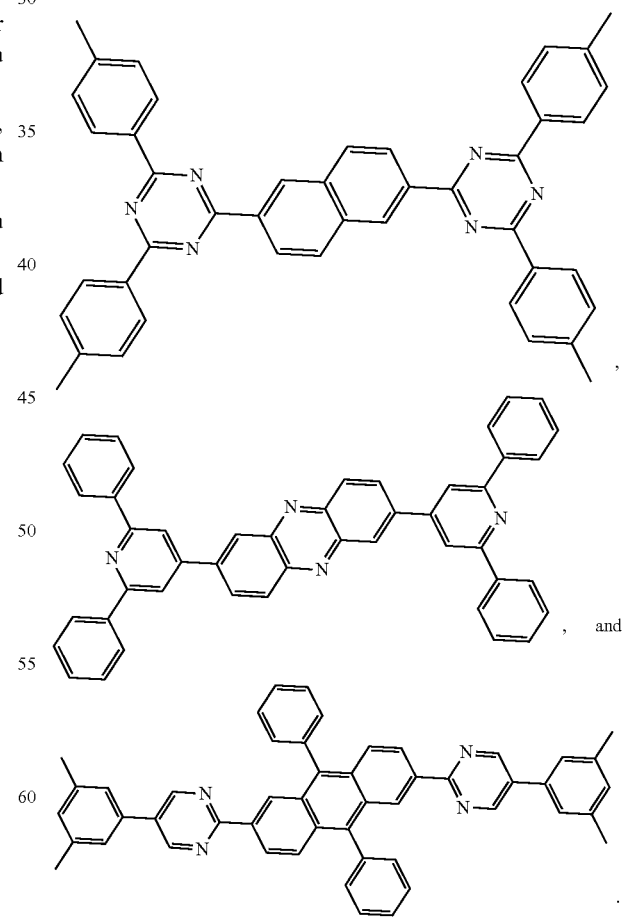

Preferably, the first raw material is present in an amount of 2.6 g to 3.4 g, and the first raw material is present in an amount of 10 mmol; and the second raw material is present in an amount of 1.0 g to 2.1 g, and the second raw material is present in an amount of 5 mmol.

In the step 2, the deoxygenated N, N'-dimethylformamide is injected under an argon atmosphere; and reacting at 80° C. for 24 hours, cooling to room temperature, and forming a reacting solution are performed.

In the step 4, dichloromethane and n-hexane are added, a volume ratio of dichloromethane and n-hexane is 1:3, and purifying by column chromatography is performed.

In the step 3, the reacting solution is poured into 200 ml ice water, extracting with dichloromethane for three times is performed, and combing an organic phase and filling silica gel into a column are performed.

In first embodiment, synthesis route of target compound I:

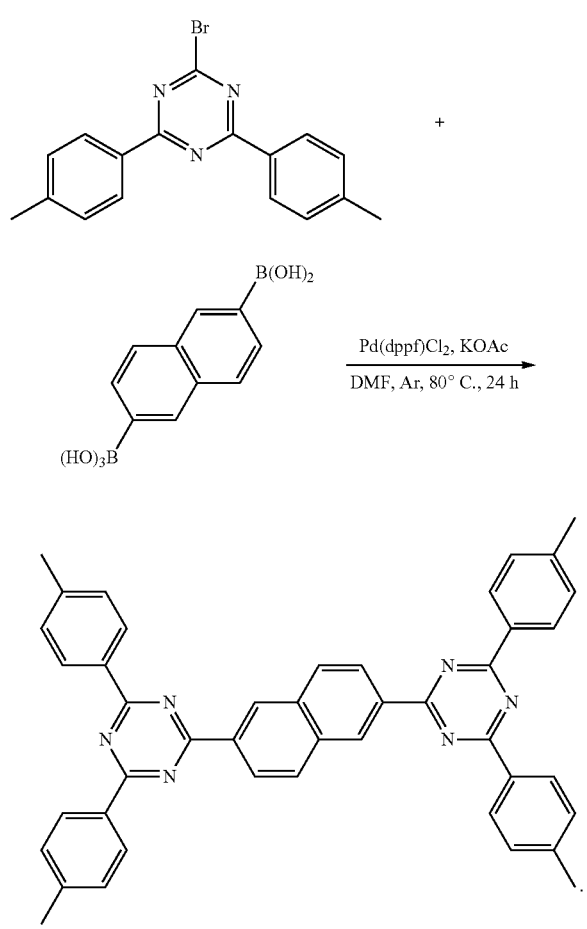

A first raw material comprising a $R_1$ group is

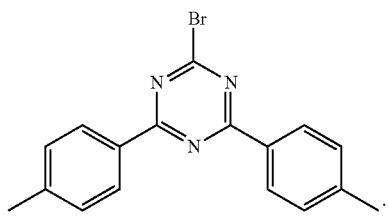

A second raw material comprising a $R_2$ group is

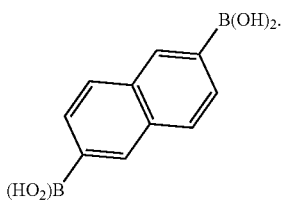

The first raw material, the second raw material, Pd(dppf)Cl$_2$, and potassium acetate are mixed.

Synthesis Steps:
The raw material

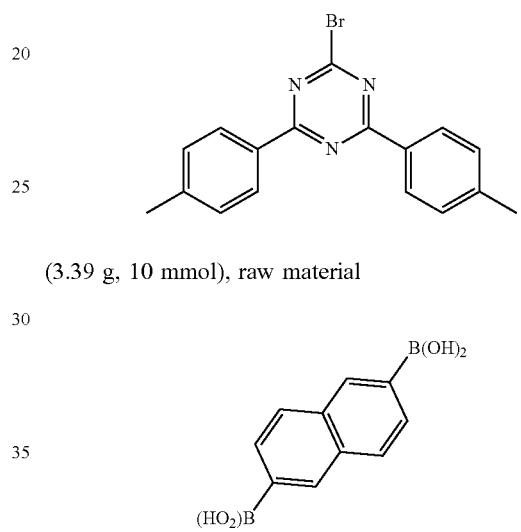

(3.39 g, 10 mmol), raw material (1.08 g, 5 mmol), Pd(dppf)Cl$_2$ (0.36 g, 0.4 mmol), and potassium acetate (0.12 g, 1.2 mmol) are added into a 250 mL two-necked bottle. (0.12 g, 1.2 mmol). Then, vacuuming for three times is performed, and the deoxygenated N, N'-dimethylformamide is injected under an argon atmosphere; and it is reacted at 80° C. for 24 hours. Next, cooling to room temperature and forming a reacting solution are performed. The reacting solution is poured into 200 ml ice water, extracting with dichloromethane for three times is performed, and combing an organic phase and filling silica gel into a column are performed. Dichloromethane and n-hexane are added. A volume ratio of dichloromethane and n-hexane is 1:3, and purifying by column chromatography is performed. A white powder presented in an amount of 2.17 g is obtained, and a yield is 67%. MS (EI) m/z: 646.18.

In second embodiment, synthesis route of target compound II:

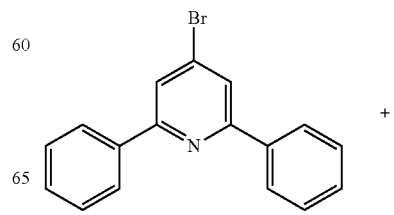

-continued

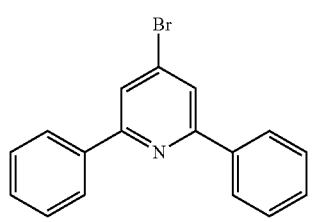

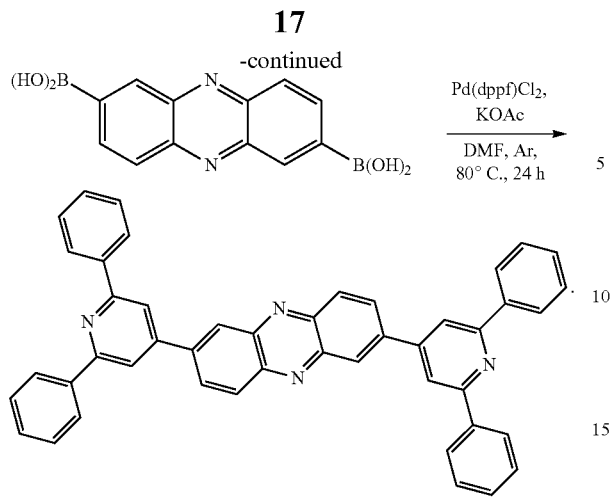

A first raw material comprising a R₁ group is

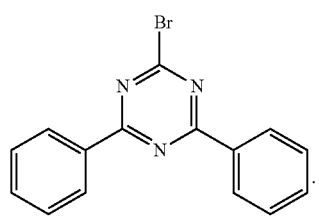 [SMILES: Brc1nc(-c2ccccc2)nc(-c2ccccc2)n1]

A second raw material comprising a R₂ group is

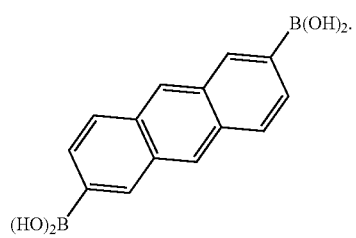 [SMILES: OB(O)c1ccc2cc3cc(B(O)O)ccc3cc2c1]

Synthesis Steps:
The raw material

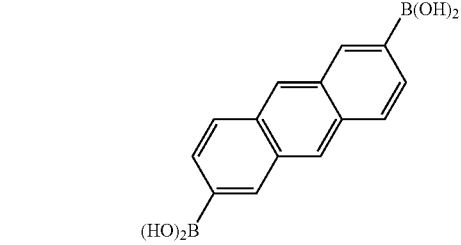 [SMILES: OB(O)c1ccc2cc3cc(B(O)O)ccc3cc2c1]

(3.09 g, 10 mmol), raw material (1.33 g, 5 mmol), Pd(dppf)Cl₂ (0.36 g, 0.4 mmol), and potassium acetate (0.12 g, 1.2 mmol) are added into a 250 mL two-necked bottle. (0.12 g, 1.2 mmol). Then, vacuuming for three times is performed, and the deoxygenated N,N'-dimethylformamide is injected under an argon atmosphere; and it is reacted at 80° C. for 24 hours. Next, cooling to room temperature and forming a reacting solution are performed. The reacting solution is poured into 200 ml ice water, extracting with dichloromethane for three times is performed, and combing an organic phase and filling silica gel into a column are performed. Dichloromethane and n-hexane are added. A volume ratio of dichloromethane and n-hexane is 1:3, and purifying by column chromatography is performed. A white powder presented in an amount of 2.00 g is obtained, and a yield is 63%. MS (EI) m/z: 638.21.

In third embodiment, synthesis route of target compound III:

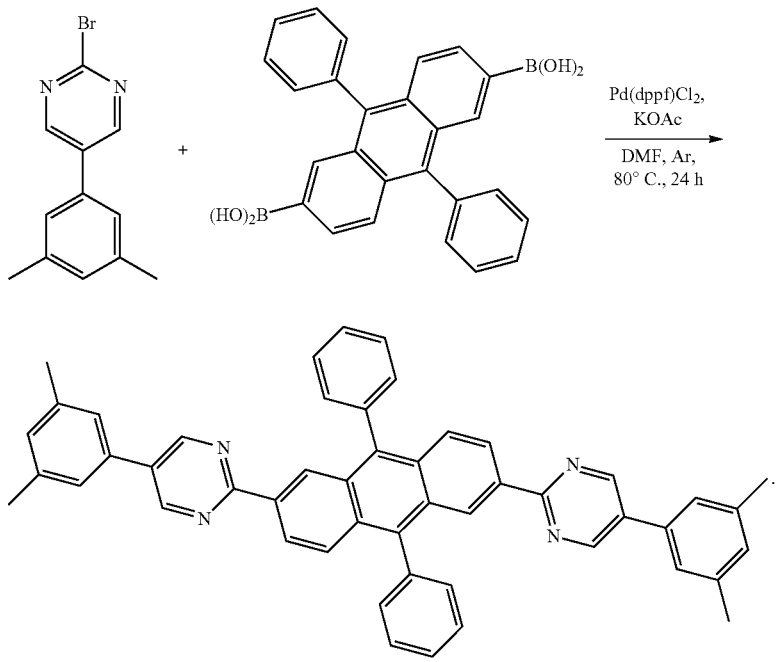

A first raw material comprising a R₁ group is

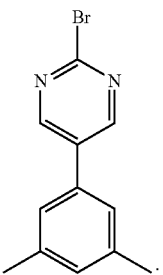

A second raw material comprising a R₂ group is

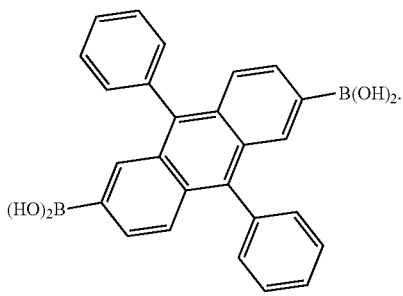 [SMILES: OB(O)c1ccc2c(-c3ccccc3)c3cc(B(O)O)ccc3c(-c3ccccc3)c2c1]

The first raw material, the second raw material, Pd(dppf)Cl₂, and potassium acetate are mixed.

Synthesis Steps:

The raw material

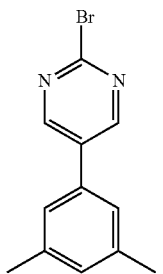

(2.62 g, 10 mmol), raw material

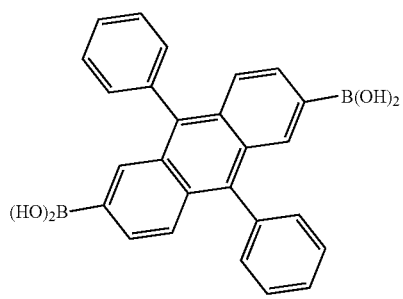 [SMILES: OB(O)c1ccc2c(-c3ccccc3)c3cc(B(O)O)ccc3c(-c3ccccc3)c2c1]

(2.09 g, 5 mmol), Pd(dppf)Cl₂ (0.36 g, 0.4 mmol), and potassium acetate (0.12 g, 1.2 mmol) are added into a 250 mL two-necked bottle. Then, vacuuming for three times is performed, and the deoxygenated N, N'-dimethylformamide is injected under an argon atmosphere; and it is reacted at 80° C. for 24 hours. Next, cooling to room temperature and forming a reacting solution are performed. The reacting solution is poured into 200 ml ice water, extracting with dichloromethane for three times is performed, and combing an organic phase and filling silica gel into a column are performed. Dichloromethane and n-hexane are added. A volume ratio of dichloromethane and n-hexane is 1:3, and purifying by column chromatography is performed. A white powder presented in an amount of 2.11 g is obtained, and a yield is 61%. MS (EI) m/z: 694.89.

Referring to FIG. 1, a top-emitting device is provided, and a photocoupling output layer is made of an N heterocyclic planar photocoupler output material. The top-emitting device includes: a substrate 1, a hole injection layer 2, a hole transport layer 3, an electron blocking layer 4, a light emitting layer 5, a hole blocking layer 6, an electron transport layer 7, an electron injection layer 8, a translucent electrode 9, and a photocoupling output layer 10.

The substrate 1 made of a glass and a total reflection (ITO/Ag/ITO) substrate, and Ag is a reflective surface, so that the light emitted from a top surface of device.

The hole injection layer 2 is used to inject holes from ITO to the OLED device and is made of MoO₃.

The hole transport layer 3 is used to transport the injected holes, and at the same time, by adjusting its thickness, it may play a role of adjusting the resonant wavelength of the microcavity.

The electron blocking layer 4 blocks electrons in the light emitting layer, prevents the electrons from being transported to the hole transport layer, and restricts the recombination region of the exciton in the light emitting layer.

The light emitting layer 5 is used for recombining the holes and electrons to generate excitons, so that the fluorescent material emits light under the action of the excitons.

The hole blocking layer 6 blocks holes in the light emitting layer, prevents the holes from being transported to the electron transport layer, and restricts the recombination region of the exciton in the light emitting layer.

The electron transport layer 7 transports the injected electrons.

The electron injection layer 8 injects electrons into the OLED device, and is generally Yb or LiF.

The translucent cathode layer 9 is used for translucent emission and transmission, can adjust the strength of the microcavity, and is made of a magnesium/silver translucent electrode.

The photocoupling output layer is provided the present invention, and it is used for coupling and extracting light to improve the light output efficiency.

The performance data of the device are shown in the following table:

| Device | CPL material | Maximum current efficiency (cd/A) | (CIEx, CIEy) | Maximum external quantum efficiency (%) |
| --- | --- | --- | --- | --- |
| Device 1 | Compound 1 | 6.8 | (0.13, 0.048) | 14.3% |
| Device 2 | Compound 2 | 6.7 | (0.13, 0.046) | 14.1% |
| Device 3 | Compound 3 | 7.2 | (0.13, 0.047) | 14.9% |

The above data shows that the higher the "N" value, the higher the corresponding maximum current efficiency reflected in the OLED device. The "n" value is the refractive index. The planarity of the target compound is Compound 3>Compound 1>Compound 2. The relationship between the "n" value and the planarity is consistent, which indicates that the molecule corresponding to high planarity has a high refractive index.

The "N" value of the photocoupler output material in the prior art is generally below 1.9 at 460 nm. The "N" value of the material of the present invention is greater than 1.95 at 460 nm. Because the "n" value is increased, the thickness of the photocoupling output layer is reduced. Therefore, the device efficiency is improved.

In the above, the present application has been described in the above preferred embodiments, but the preferred embodiments are not intended to limit the scope of the invention, and a person skilled in the art may make various modifications without departing from the spirit and scope of the application. The scope of the present application is determined by claims.

What is claimed is:

1. An N heterocyclic planar photocoupler output material selected from any one of the following formula structures:

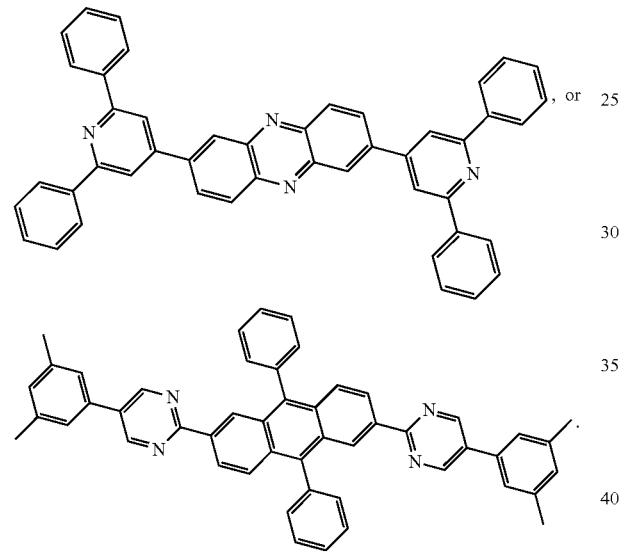

2. The N heterocyclic planar photocoupler output material according to claim 1, wherein synthetic raw materials for the N heterocyclic planar photocoupler output material comprise a first raw material comprising a $R_1$ group and a second raw material comprising a $R_2$ group;

wherein the first raw material comprising the $R_1$ group is selected from any one of the following formula structures:

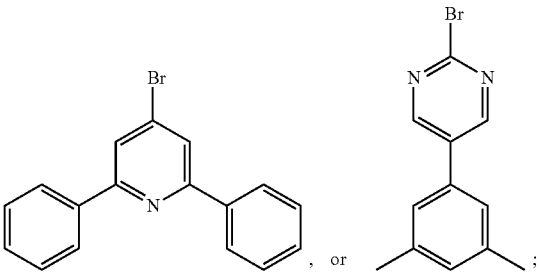

and wherein the second raw material comprising the $R_2$ group is selected from any one of the following formula structures:

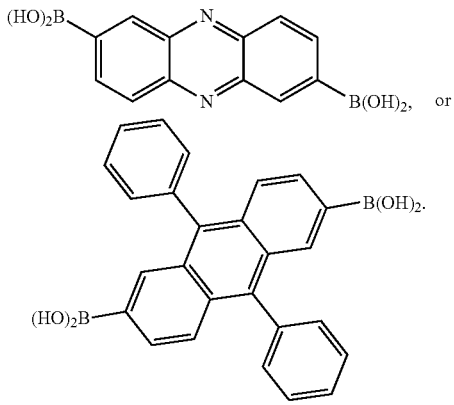

* * * * *